United States Patent [19]

Neumann

[11] 4,120,397
[45] Oct. 17, 1978

[54] UNIT FOR ACCOMMODATING DISPOSABLE BLADELIKE ARTICLES

[75] Inventor: Arthur E. Neumann, Winnetka, Ill.

[73] Assignee: Richard-Allan Medical Industries, Inc., Richland, Mich.

[21] Appl. No.: 839,387

[22] Filed: Oct. 4, 1977

[51] Int. Cl.² .......................... B65D 25/00; B65F 7/00; A61B 19/02; A61F 13/00
[52] U.S. Cl. .................................. 206/370; 206/356; 206/45.2
[58] Field of Search ............... 206/370, 205, 366, 438, 206/63.5, 527, 359, 350, 354, 356, 45.2; 312/209; 232/43.1

[56] References Cited
U.S. PATENT DOCUMENTS

| | | | |
|---|---|---|---|
| 2,000,681 | 5/1935 | Weller | 206/45.2 |
| 2,034,006 | 3/1936 | Smith | 206/63.5 |
| 3,002,607 | 10/1961 | Laverty | 206/356 |
| 3,348,894 | 10/1967 | De Berry | 312/209 |
| 3,481,462 | 12/1969 | Chapel | 206/438 |
| 3,876,067 | 4/1975 | Schwarz | 206/205 |
| 3,944,069 | 3/1976 | Eldridge, Jr. | 206/350 |
| 4,034,892 | 7/1977 | Braginetz | 206/356 |

Primary Examiner—William T. Dixson, Jr.
Attorney, Agent, or Firm—Neuman, Williams, Anderson & Olson

[57] ABSTRACT

A unit is provided for accommodating various disposable articles, such as used surgical blades and the like, wherein each article is automatically removed from the tang of a handle and retained within a receptacle. The removal of the article from the tang is accomplished without physical contact between the article and the person utilizing the unit. The receptacle is provided with at least one elongated article-accommodating compartment accessible only through an entry formed at an end thereof. The entry is sized so as to permit the tang and attached article to be manually inserted therethrough into the compartment. Upon the tang being withdrawn from the compartment through the entry the article is automatically removed therefrom and remains entrapped within the compartment.

15 Claims, 19 Drawing Figures

UNIT FOR ACCOMMODATING DISPOSABLE BLADELIKE ARTICLES

BACKGROUND OF THE INVENTION

In present surgical procedure, each scalpel or the like normally includes a reusable handle having a tang on which is mounted a replaceable blade. The handle per se is normally subjected to repeated sterilization and thus is reusable; whereas, the blade is used once and then disposed of. Each blade is provided with a suitable slot formed therein which is adapted to slidably accommodate and interlock with the handle tang. The size and shape of the cutting edge of the blade may vary over a wide range and will depend upon the type of surgery to be performed. The interconnection between the blade and tang is such that the slotted blade portion must be distorted slightly relative to the tang when the blade is being assembled on or disassembled from the tang.

After use, the blade is soiled and becomes difficult, awkward and hazardous for the nurse or attendant to manually remove same from the tang. Furthermore, at the conclusion of the surgery it is imperative that all used and unused blades be accounted for. Thus, to meet such requirements, a systematic expeditious and reliable procedure must be followed.

In addition to blades, numerous items such as disposable needles of preselected sizes and shapes are utilized and must be strictly accounted for during and at the conclusion of the surgery. To facilitate an accurate count, it is desirable to keep the used needles in an exposed yet safe location within a given area and separated from one another.

Also, during the course of the surgery, a substantial amount of sundry articles or trash is generated by opened sterile packages, enclosures, wrappings and the like. As in the case of the used blades and needles, it is important that such trash be accounted for and contained in an orderly manner for disposal.

Various devices and systems have hereto been proposed in an effort to meet the stringent requirements for accounting and disposal of the various used blades, needles and sundry articles. Such prior devices and systems, however, have been beset with one or more of the following shortcomings: (a) the device was of complex, bulky construction; (b) the device was awkward and frustrating to manipulate; (c) the device was not readily disposable and did not effectively retain the used articles in such a way that they could be readily accounted for without physically touching the article; (d) the device was incapable of accommodating a variety of soiled articles; and (e) the device was incapable of automatically removing a blade or like article from the tang of a handle and then entrapping the removed blade in a convenient, yet safe, manner within a compartment.

SUMMARY OF THE INVENTION

Thus, it is an object of the invention to provide a unit of the type described which avoids all of the aforenoted shortcomings.

It is a further object of the invention to provide a unit of the type described wherein the components thereof are lightweight, compact and inexpensive to produce.

It is a further object of the invention to provide a unit of the type described having a component thereof which permits a used bladelike article to be automatically removed from the tang of a handle without requiring physical contact between the used article and the person utilizing the device, and once the article has been removed to cause same to be permanently entrapped in safe, convenient manner within a compartment.

Further and additional objects wil appear from the description, accompanying drawings and appended claims.

In accordance with one embodiment of the invention a unit, sometimes referred to as a kit, is provided which comprises a receptacle provided with at least one elongated article-accommodating cmpartment accessible only through an entry formed at an end thereof. The entry is of such a size that it will permit a tang and an attached article to be inserted therethrough into the compartment. Upon entering the compartment the attached article engages cam means and is distorted thereby so that when the tang is withdrawn from the compartment through the entry, the distorted article will abut a portion of the receptacle and be automatically disassembled from the tang causing the article to become entrapped within the compartment. The entrapped article may be readily accounted for by observing same through a transparent portion of the receptacle.

DESCRIPTION

For a more complete understanding of the invention reference should be made to the drawings wherein:

FIGS. 8A–8C are similar to FIG. 7 but showing respectively the tang and attached blade partially inserted into the compartment; fully inserted into the compartment; and with the blade being automatically disassembled from the tang, as the latter is being manually withdrawn from the compartment through the entry; FIG. 8C also shows in section a plurality of used needles attached to the exterior of the receptacle.

Figure 1:
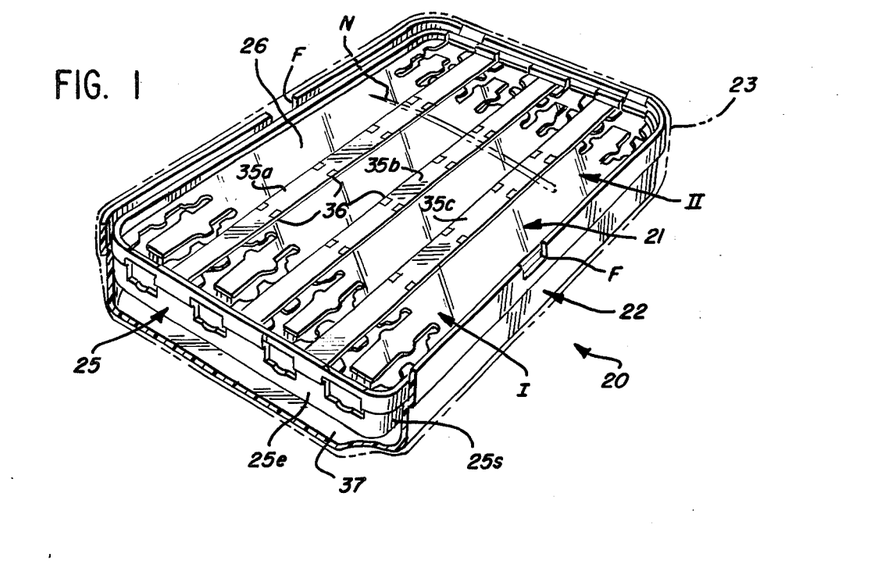
FIG. 1 is a fragmentary perspective view, partially in vertical section, of one form of the unit and showing the receptacle and traylike member thereof in nested relation and disposed within an outer protective wrapping, the latter being shown in phantom lines.

Referring now to the drawings and more particularly to FIG. 1, one form of the improved unit 20 is shown which includes a receptacle 21, a traylike member 22 in which the receptacle is initially nested, and an outer protective wrapping 23 (e.g., a peel-away sheath; a vacuum formed blister-type membrane; or the like). The receptacle and member in a compact nested relation are assembled within the protective wrapping and then the components 21, 22 are subjected to sterilization.

Prior to the commencement of surgery, the nested receptacle and member are removed from the protective wrapping, placed within the sterilized zone or area wherein the surgery is to be performed, and then the receptacle 21 and member 22 are separated from one another and placed in convenient locations (see FIG. 2) within the zone.

Figure 3:
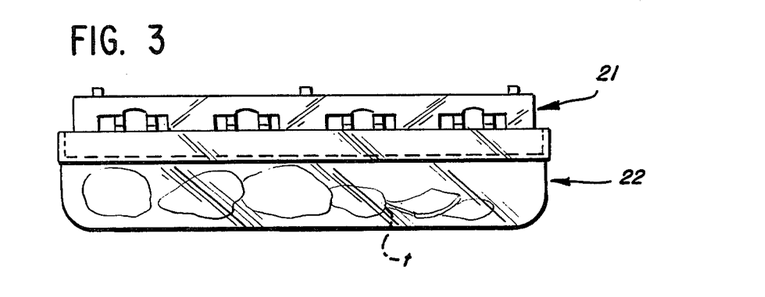
FIG. 3 is an end view of the components of FIG. 2 shown assembled in inverted relation ready for disposal.

At the conclusion of the surgery and, after the various used blades B, needles N (see FIG. 8C), and trash t have been collected within and/or attached to the receptacle and traylike member and accurately accounted for, the receptacle and traylike member are reassembled in inverted relation, as seen in FIG. 3, and then appropriately disposed of in accordance with prevailing sanitary rules and regulations.

Figure 6:
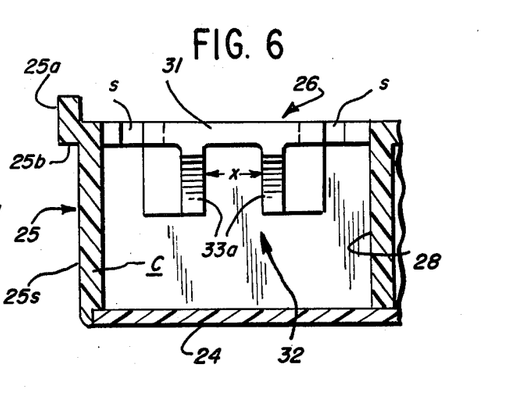
FIG. 6 is a sectional view taken along line 6—6 of FIG. 4.

Receptacle 21 may take various forms and shapes and will depend in part upon the number, style and type of blades likely to be used in the course of performing the surgery. The receptacle 21, shown in FIG. 1, is particularly suitable for accommodating eight used blades B in a manner to be hereinafter described. The number and arrangement of the compartments C formed in the receptacle may vary from that illustrated without departing from the scope of the invention hereinafter described and claimed. Receptacle 21 is preferably formed of a rigid transparent thermoplastic material and includes a bottom panel 24, an upright wall 25 delimiting same, and a top panel 26. The outer perimeter of top panel 26 is delimited by an upright flange 25a (see FIGS. 2 and 6).

The receptacle 21, as seen in FIG. 1 is provided with eight interior blade-accommodating compartments, which are arranged in two parallel rows I and II of four compartments each. Thus, corresponding compartments of each row are disposed in end-to-end relation and are separated by a common partition 27 (see FIG. 7). Adjacent compartments in a row are separated from one another by a common partition 28 (see FIG. 6). Partitions 27, 28 may be integral with either the top or bottom panel and extend the full distance between top panel 26 and bottom panel 24.

Upright wall 25 includes parallel opposed side sections 25s and parallel opposed end sections 25e. The aforenoted flange 25a formed on the upper portion of wall 25, is offset outwardly a slight amount so as to form a shoulder 25b (see FIG. 2).

The end sections 25e of wall 25 are each provided with four entries E aligned with corresponding compartments formed within the receptacle. Each entry E is of like configuration and includes a lower perimetric segment 30 formed in the end wall section 25e, and an upper segment 31 which is defined by an edge of top panel 26 (see FIGS. 4 and 5). Flange 25a is preferably continuous and encircles the top panel 26 for reasons to be hereinafter explained.

Figure 4:
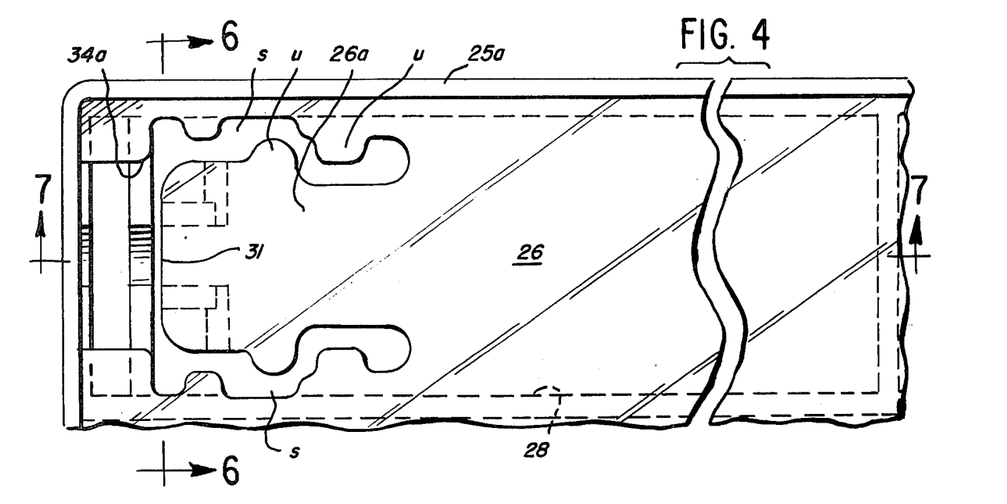
FIG. 4 is an enlarged fragmentary plan view of a corner portion of the recpetacle taken along line 4—4 of FIG. 2 and showing only one compartment formed therein.
Figure 5:
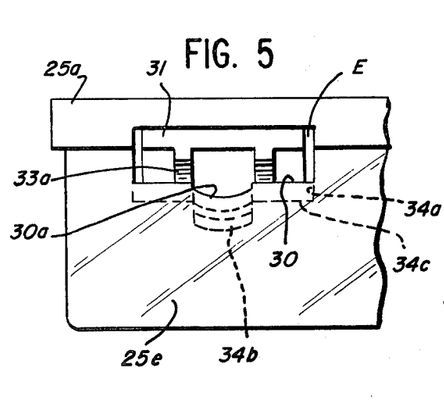
FIG. 5 is a left end elevational view of the portion of the receptacle of FIG. 4 and showing the entry formed in the end wall thereof.

As seen in FIG. 4, segmemt 31 comprises the distal end of a resilient tonguelike element 26a formed in the top panel 26. A pair of tortuous slots S separate the sides of the element from the remainder of the panel 26. The tortuous configuration of the slots S forms nodes n on the sides of the slots and thus prevents the entrapped blade from accidently sliding out through one of the slots once it has been disposed within the compartment C.

Affixed to the underside of element 26a and depending therefrom is a cam means 32. The cam means includes a pair of laterally spaced protuberances 33, each of which has a surface 33a thereof, adjacent the entry E, tapered downwardly and away from the entry (see FIG. 7). The configuration of the entry is such that it will accommodate the tang T of the handle H and the blade B attached thereto when the tang and blade are inserted through the entry into the compartment C (see FIG. 8A), as will be described more fully hereinafter.

The spacing X between the protuberances 33 of the cam means 32 (see FIG. 6) is such that only the tang T of the handle H will pass therethrough as the tang is inserted into or withdrawn from the compartment C.

Figure 7:
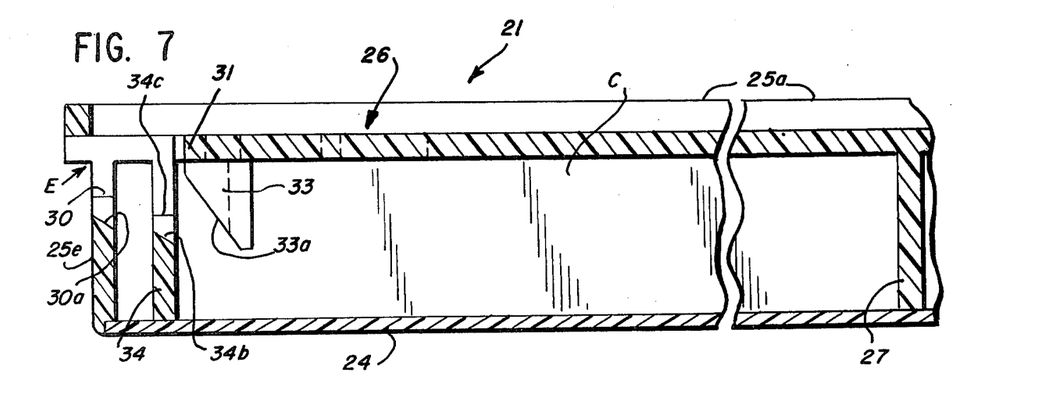
FIG. 7 is a fragmentary sectional view taken along line 7—7 of FIG. 4.

As seen in FIG. 7, there may be disposed inwardly of wall end section 25e, an upright panel 34 which extends between the bottom panel 24 and underside of top panel 26. Panel 34 is substantially parallel to end section 25e and is provided with an opening 34a which is aligned with but slightly larger than the interruption formed in the wall end section. A portion 34b of opening 34a is recessed a slight amount and is beveled downwardly (see FIG. 7). The perimetric segment 30 of the interruption formed in wall end section 25e is also provided with a recessed portion 30a which is beveled downwardly in substantially the same manner as portion 34b of panel 34.

It will be noted in FIG. 7 that the beveled surfaces 30a and 34b are disposed in substantially the same inclined plane. The beveled recessed portions of end section 25e and panel 34 are adapted to accommodate the portion Ta of the tang T which extends beneath the attached blade B (see FIGS. 8A and 8C) when the tang is passing through the entry E.

Figure 8A:
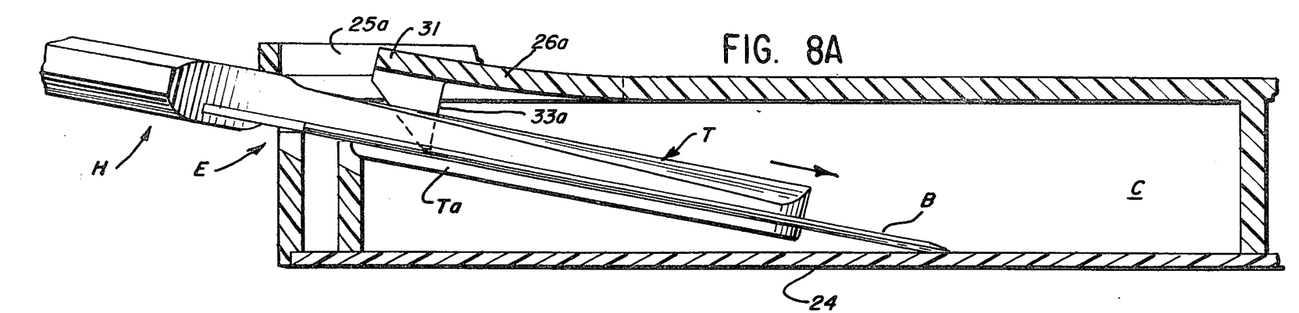
Figure 8B:
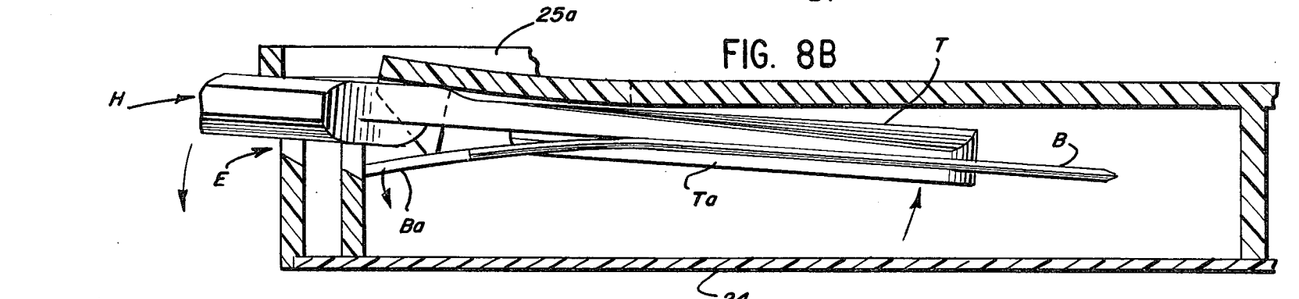
Figure 8C:
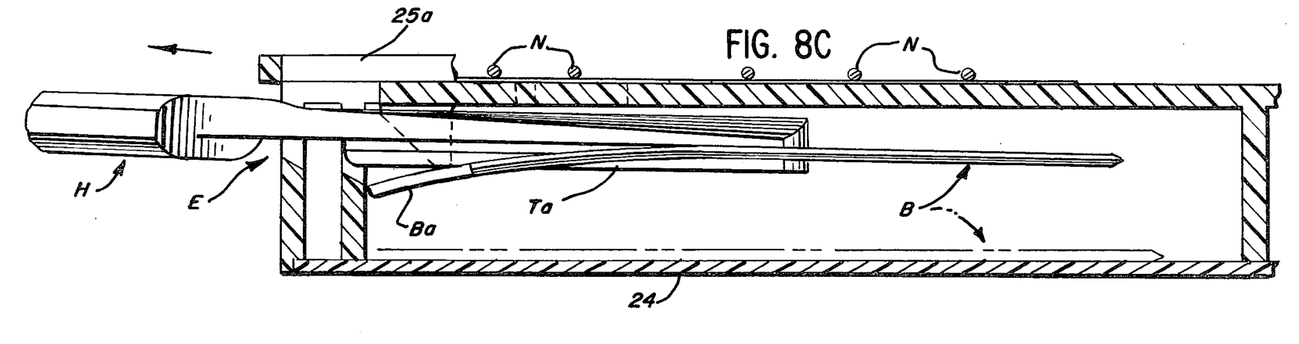

As seen in FIG. 8A, when the tang T and attached blade B are initially inserted through the entry, the blade B and tang portion Ta are manipulated so as to pass beneath the cam means protuberances. Because the underside of the blade slidably engages the portions of perimetric segment 30 disposed on opposite sides of the recess 30a, the blade upperside will engage the ends of the protuberances and cause the tonguelike element 26a to be resiliently deflected upwardly a slight amount. Once the tang and attached blade have been inserted into the compartment a sufficient amount so that the trailing end Ba of the blade passes inwardly of panel 34, the trailing end of the blade will be deflected downwardly relative to the tang underside by the force of the tonguelike element 26a so that the trailing edge of the blade will be below the portions 34c of the opening 34a disposed on opposite sides of the recess 34b (see FIGS. 5 and 8B). Once the trailing edge Ba of the blade B has assumed the deflected position, the trailing edge will abut the inside surface of panel 34 as the tang T is being withdrawn from the compartment. Because of the deflected condition of the trailing end of the blade, the tang portion Ta will slide endwise out of the slot formed in the blade itself and effect disassembly of the blade and tang. The disassembled blade will remain within the compartment after the tang has been withdrawn from the receptacle. The slotted blade and the tang are of conventional designs and per se form no part of the claimed invention.

Because of the depending cam protuberances and the tortuous configuration of the slots S, the entrapped blade will remain inaccessible within the compartment notwithstanding that the receptacle is subjected to abusive handling. The preferred practice with receptacle 21 is to entrap only one used blade in each compartment thereby facilitating accounting of the used blades during and at the conclusion of the surgery. The top panel 26 is preferably formed of transparent material thereby enabling the entrapped blade to be readily observed.

It is important to note the receptacle 21 embodies various structural features which enable the used blade to be readily disassembled from the tang while the blade is completely disposed within the compartment. This feature effectively removes the hazards normally associated with blade removal in that no physical contact between the blade and the fingers of the person utilizing the receptacle is required.

Figure 12:
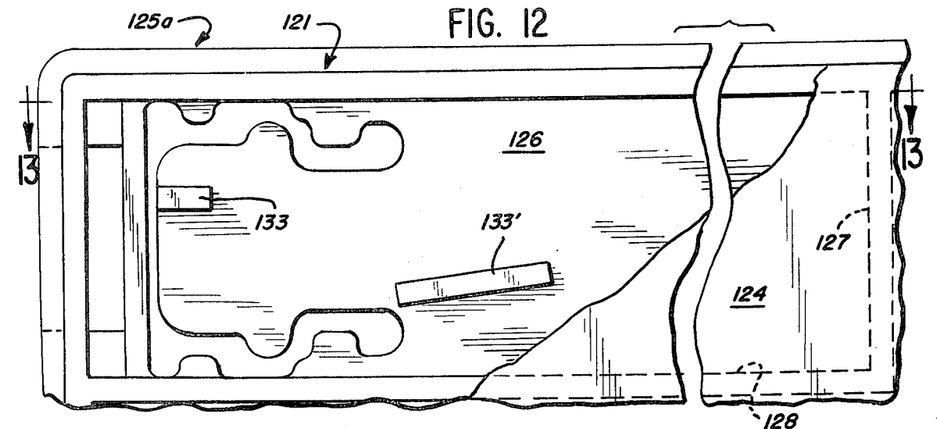
FIG. 12 is a fragmentary bottom view of a second form of receptacle with the bottom panel thereof removed so as to expose the cam means protruding downwardly from the top panel into the compartment.
Figure 13:
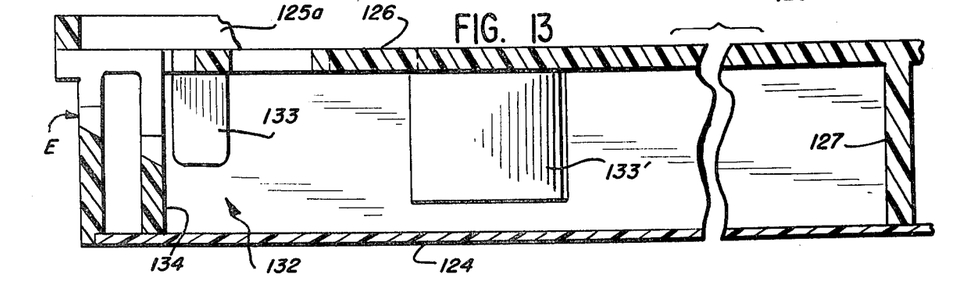
FIG. 13 is a fragmentary sectional view taken along line 13—13 of FIG. 12.

FIGS. 12, 13 illustrate a modified form of receptacle 121 which differs from receptacle 21 only with respect to the cam means 132 wherein a single protuberance 133 is disposed adjacent the entry E and depends from the top panel 126. A second depending protuberance 133' is also provided which is spaced inwardly from protuberance 133 and is disposed slightly askew (see FIG. 12). Protuberance 133 resiliently engages a portion of the attached blade disposed to one side of the tang and causes the trailing end portion of the blade to be deflected downwardly relative to the tang a sufficient amount so that the trailing end portion will abut the inner panel 134 when the tang is withdrawn. The second protuberance 133' serves to guide the leading end portion of the inserted blade, so that the tang will be in proper alignment with the entry E for withdrawal. The arrangement of the protuberances 133 and 133' have been found to be particularly suitable for relatively narrow blades.

Figure 14:
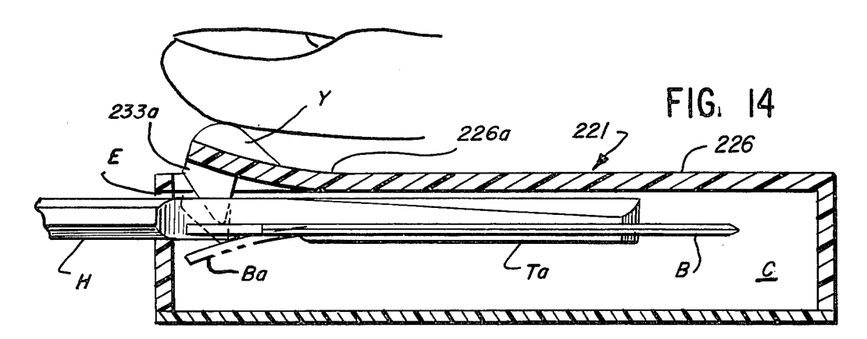
FIG. 14 is a fragmentary section view, similar to FIG. 8A, of a third form of receptacle and showing the relative disposition of the tang and attached blade with respect to the cam means as the tang and blade are being inserted into the compartment through the entry thereto.

FIG. 14 discloses a modified receptacle 221 which embodies numerous structural features incorporated in receptacle 21. Accordingly, like features in receptacle 221 are identified by the same numerals as receptacle 21 except in the two hundred series. The principal difference between receptacles 21 and 221 is that in receptacle 221, the segment 226a, to which the cam protuberances 233a extend, is formed so as to have a normal, upwardly bowed configuration with respect to the top panel 226 whereby the protuberances do not extend into the compartment C unitl manually depressed. A button Y may be provided on the exterior of segment 226a to facilitate depressing thereof when desired. The segment 226a is depressed only, after the tang and attached blade have been inserted into the compartment a sufficient amount so that the trailing end Ba of the blade has cleared the end wall of the receptacle in which the entry E is formed. The segment 226a remains manually depressed while the tang is withdrawn endwise from the compartment and the detached blade remains entrapped within the compartment.

Figure 15:
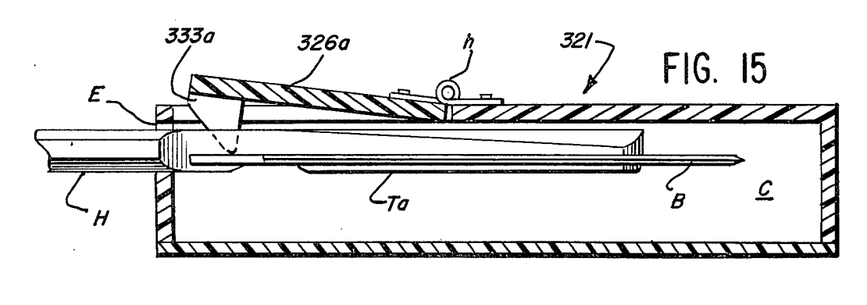
FIG. 15 is similar to FIG. 14 but showing a fourth form of receptacle.

FIG. 15 illustrates a modified receptacle 321 which is similar to receptacle 221, except that segment 326a is connected to the top panel 326 by a hinge h. The hinge is spring-biased so that segment 326a normally assumes a raised position (see FIG. 15) wherein the cam protuberances 333a formed on the segment do not extend into the compartment C.

Figure 16:
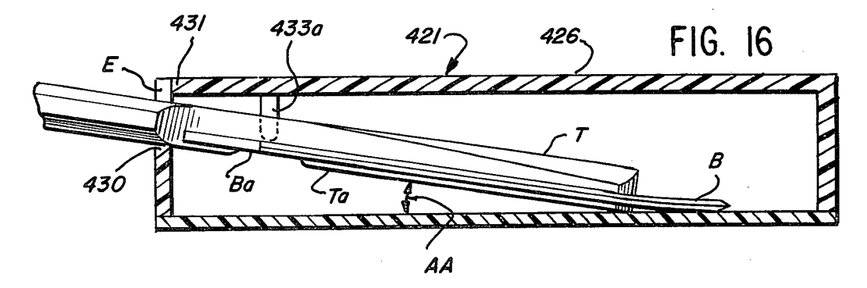
FIG. 16 is similar to FIG. 14 but showing a fifth form of receptacle.
Figure 17:
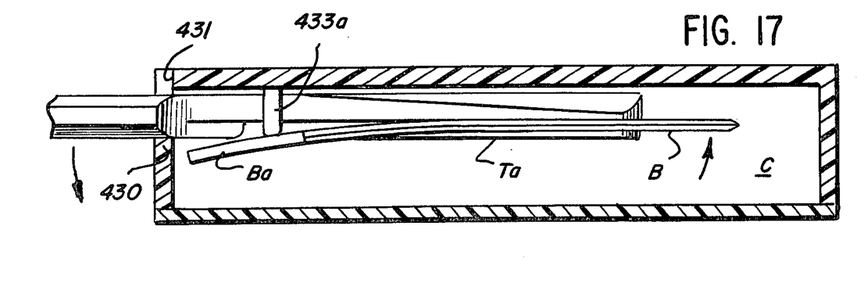
FIG. 17 is the same as FIG. 16 but showing the relative position of the tang and attached blade with respect to the cam means just prior to the tang being withdrawn from the compartment.

FIGS. 16-17 illustrate another modified receptacle 421, wherein in lieu of a segment, the cam protuberances 433a extend downwardly from the top panel 426 and assume a stationary position at all times. The protuberances 433a are spaced inwardly a substantial amount from the end wall of the receptacle in which the entry E is formed. The depth of the compartment formed in receptacle 421 is greater than in the previously described receptacles, so that the tang and attached blade may be initially inserted through the entry into the compartment and beneath protuberances 433a a sufficient amount so that the trailing end portion Ba of the attached blade will clear the end wall of the compartment and be aligned beneath the protuberances 433a. To effect such positioning of the attached blade it is necessary that the tang and attached blade be inserted at an inclined angle AA (see FIG. 16). Once the tang and blade have been inserted into the compartment the required amount, the handle H is manually pivoted in a counterclockwise direction about a perimetric segment 430 of the entry as a fulcrum to a substantially horizontal position whereupon the depending stationary protuberances 433a will cause the trailing edge Ba of the blade to be distorted downwardly, as shown in FIG. 17. While the handle remains in a substantially horizontal position, the tang thereof is withdrawn from the compartment causing the distorted trailing end of the blade to abut the end wall of the compartment and the blade to be removed endwise of the withdrawing tang.

It should be noted, for purposes of clarity, that receptacles 221, 321 and 421 do not show double panels at the entry nor periphery flanges delimiting the top panels or various other structural features embodied in receptacle 21; however, such features may be included if desired. Furthermore, receptacles 221, 321, 421 may be provided with a plurality of compartments rather than the single compartment as shown.

It will be noted in FIG. 1 that the exposed surface of the top panel 26 of the receptacle 21 is provided with a plurality of strips 35a, b, and c which are of magnetic material. Each strip is affixed to the exposed surface by suitable means and is provided with a plurality of longitudinally spaced peripheral notches which are adaped to receive lugs 36 formed on the surface. The lugs retain the strips in proper spaced parallel relation. It is preferred that the strips 35a-b be aligned with the partitions 28 (see FIGS. 4, 6) which separate the adjacent compartments of a row I or II. Similar magnetic strips may be utilized with receptacles 121, 221, 321 and 421.

The strips serve to hold needles N and similar ferrous metal articles in selected, separate positions on the exposed surface of the top panel. One such needle is shown in phantom lines in FIG. 1. Because the needles may vary in length and shape, the number of strips contacted by a given needle may vary from that shown. The peripheral flange 25a, which delimits the top panel 26, provides protection against the ends of the needle accidentally piercing a person or their wearing apparel.

Figure 2:
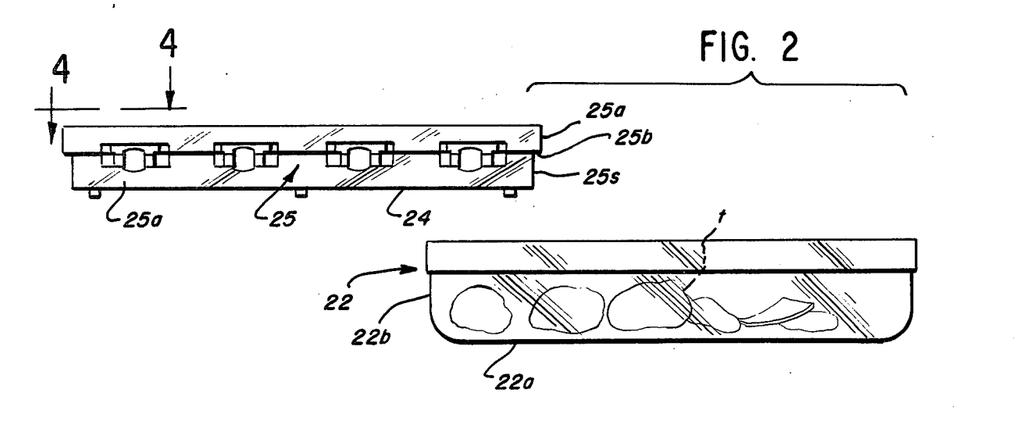
FIG. 2 is an end view of the receptacle and traylike member of FIG. 1 disposed in disassembled relation and showing, in dotted lines, trash contained within the traylike member.
Figures 9, 10, 11:
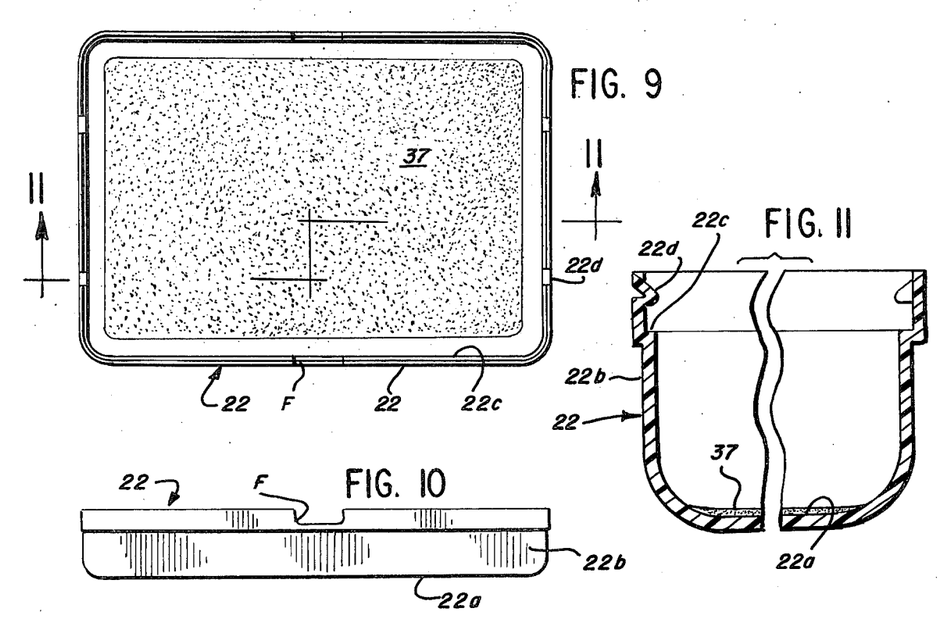
FIG. 9 is a top plan view of the traylike member of FIG. 2.
FIG. 10 is a side elevational view of the traylike member of FIG. 9.
FIG. 11 is an enlarged fragmentary sectional view taken along line 11—11 of FIG. 9.

FIGS. 9–10 reveal the structural details embodied in one form of the traylike member 22, shown in FIGS. 1 and 2. Member 22 is preferably of one piece construction and formed from an inexpensive, disposable plastic material. Member 22 includes a bottom section 22a which closely approximates the configuration of the bottom panel 24 of the receptacle 21. The inner surface of bottom section 22a is provided with a coating 37 of suitable tacky, non-drying material (e.g. a synthetic resin emulsion, pressure-sensitive adhesive — Swift #46363). It will be noted in FIG. 1 that, when receptacle 21 and the traylike member 22 are in nested relation, the bottom section 22a and the coating 37 thereon are spaced from the underside of the receptacle bottom panel 24.

Delimiting the bottom section 22a and extending upwardly therefrom is a continuous wall 22b which includes side and end sections corresponding closely to those of the receptacle. The height of the wall 22b is greater than the height of the receptacle wall and, thus, assures a spacing of the receptacle bottom panel from the coating 37 when the components are in nested relation (see FIG. 1). The upper portion of the wall 22b is offset outwardly so as to form an interior ledge 22c (see FIG. 11). The ledge is adapted to supportingly engage the exterior shoulder 25b formed in the wall of the receptacle (see FIG. 2) when the receptacle is nested within the member 22. The ledge 22c also limits the extent to which the receptacle 21 and member 22 can be pushed together when they are in inverted relation. As a further means of maintaining the bottom panel of the receptacle in proper spaced relation with coated bottom section of the traylike member when the latter and receptacle are in nested relation, an upwardly projecting spacer rib, not shown, may be provided on the inner surface of the bottom section of the member 22. Such a rib would engage the underside of the receptacle and prevent jamming together of the receptacle and member. A plurality of finger cutouts or slots F may be formed in the offset upper portion of the wall 22b so as to facilitate denesting of the receptacle and traylike member.

In addition to the ledge 22c, the interior surface of the upper portion of the wall 22b is provided with a plurality of spaced inwardly projecting nubs 22d. The nubs are adapted to lock into suitable recesses, not shown, formed in the exterior surface of the peripheral flange 25a which surrounds the top panel 26 of the receptacle, only when the latter and the traylike member 22 are in inverted relation (see FIG. 3).

When the components 21 and 22 are separated from one another, as seen in FIG. 2, the member 22 is adapted to collect on the coated surface thereof, various articles of trash which are normally generated in the course of the surgery (e.g., discarded wrappers for sterilized articles, such as blades or the like). Because of the tacky character of the coating 37, the articles of trash will remain adhered to the bottom section of the traylike member 22, notwithstanding that the latter may assume an inverted position with respect to the receptacle. The inverted positioning of the receptacle and traylike member, normally occurs at the conclusion of the surgery and after the blades, needles and articles of trash have been accounted for. The assembled inverted components may then be suitably disposed of in accordance with the rules of the hospital, clinic or the like governing the disposal of such articles. The traylike member 22 may be used in the same manner as described with respect to modified receptacles 121, 221, 321 and 421.

While the receptacles 21, 121, 221, 321 and 421 have been described for use in disposing of surgical blades, it is to be understood that it is not intended to be so limited. For example, such receptacles may be used to remove wood-carving blades or the like from tangs. In this latter instance, sterilization of the unit is not required. Furthermore, the movement of the tang and attached blade to effect distortion of the blade from the tang has heretofore been described as pivoting and horizontal; however, in certain instances it might require a twisting movement followed by a horizontal movement. This latter sequence of manipulations will depend upon the arrangement and configuration of the cam protuberances and the manner in which the blade is attached to the tang.

As previously mentioned, the size and shape of the various unit components may vary over a wide range and will depend upon the circumstances surrounding the surgery to be performed. In certain instances, where there is only one row of compartments formed in the receptacle, each compartment might be provided with an entry at each end. The unit 20 under any circumstances eliminates the serious hazards associated with manually removing a used blade from a conventional scalpel handle. Furthermore, the unit enables a quick, accurate and reliable accounting of the various articles used during surgery to be made, thereby greatly facilitating the surgery procedures. The components of the unit are compact, inexpensive to produce, and may be readily disposed of when required.

I claim:

1. A disposable unit for used bladelike articles, each having a distortable trailing end portion, wherein said unit effects endwise removal of an article from the tang of a handle and permanently accommodates the removed article within the unit without physical contact between the used article and the person utilizing the unit, said unit comprising a receptacle provided with at least one interior elongated article-accommodating compartment accessible only through an entry formed in at least one end of the compartment, said entry having a configuration for permitting the tang and assembled article to be manually inserted endwise into the compartment through the entry and only the tang to be manually withdrawn endwise from the compartment through the entry subsequent to the article being removed therefrom, said entry including a first perimetric segment and a second perimetric segment in substantially opposed spaced relation with respect thereto; protruding cam means disposed within said compartment in the path of movement of the tang and assembled article and adjacent said second perimetric segment for engaging and distorting the trailing end portion of the article independently of the tang when the tang and assembled article are manually inserted endwise through the entry into the compartment, the distorted article trailing end portion abutting a fixed segment of a first compartment-forming wall and being automatically removed substantially endwise from the tang and permanently entrapped within said compartment when the tang is withdrawn from the compartment through the entry, said fixed first portion of the compartment-forming wall being adjacent to but offset from said cam means and coacting therewith to effect blockage of said entry with respect to the removed article accommodated within said compartment.

2. The unit of claim 1 wherein the cam means includes at least one protuberance extending into the compartment from a resilient segment of a second compartment-forming wall.

3. The unit of claim 2 wherein a surface of said protuberance adjacent said entry is tapered inwardly away from the entry and is adapted to slidably engage only a peripheral portion of the inserted article disposed laterally of the tang to which the article is initially attached.

4. The unit of claim 2 wherein said cam means protrudes from a resilient tonguelike element fromed in the second compartment-forming wall; the distal end of said tonguelike element being adjacent said entry and forming the second perimetric segment thereof.

5. The unit of claim 1 wherein the interior of the receptacle is provided with a plurality of individual compartments; each compartment having an entry therefor through which a tang and attached article are adapted to be manually inserted into the corresponding compartment and only the tang is adapted to be withdrawn therefrom through the entry while the article remains permanently entrapped within the corresponding compartment.

6. The unit of claim 1 wherein the first perimetric segment of said entry includes an inner panel and an outer panel spaced therefrom, said inner panel forming the fixed segment of the first compartment forming wall abutted by the distorted trailing end portion of the article when the tang is independently withdrawn from the compartment.

7. The unit of claim 1 wherein said cam means includes a pair of laterally spaced protuberances extending from a second compartment-forming wall, the spacing between said protuberances being adapted to accommodate only the width of the inserted tang, said protuberances coacting with the fixed portion of the first compartment-forming wall abutted by the distorted trailing end portion of the article to effect blockage of the entry with respect to removed article accommodated within the compartment.

8. The unit of claim 1 wherein an exterior portion of at least one wall of the receptacle is provided with means for attaching thereto a plurality of other used articles.

9. The unit of claim 8 including a traylike member adapted, when assembled with the receptacle in one relative position, to have snugly and removably nested therein the receptacle, said traylike member having a bottom section disposed in closely spaced subtending relation with an adjacent second wall of the nested receptacle; said traylike member adapted, when assembled with the receptacle in a second relative position, to be in an inverted overlying relation with respect to the said one wall of said receptacle.

10. The unit of claim 9 wherein the removable traylike member includes a wall delimiting said bottom section and extending angularly upwardly therefrom and defining an open top; said bottom section having an inner surface provided with means for attaching thereto a plurality of sundry articles, said inner surface being exposed only when said receptacle and traylike member are in disassembled relation and being in concealed spaced relation with said receptacle when the latter and said traylike member are in either assembled positions.

11. The unit of claim 10 wherein a portion of the traylike member wall defining the open top is provided with locking means adapted to releasably engage corresponding portions of said receptacle exterior when said receptacle and traylike member are in either assembled positions.

12. The unit of claim 10 wherein the attaching means on the inner surface of the bottom section of said traylike member includes a coating of tacky, non-drying material.

13. The unit of claim 1 wherein the first perimetric segment of said entry is provided with a centrally disposed recess portion adapted to accommodate a segment of the tang disposed to one side of the attached article, when the tang is moving through the entry.

14. The unit of claim 13 wherein the first perimetric segment of the entry is beveled towards the compartment and away from the second perimetric segment of the entry.

15. The unit of claim 1 wherein the protruding cam means includes at least one stationary protuberance depending from a second compartment-forming wall, the distal end of said protuberance being disposed a greater distance from a plane including said second perimetric segment than said first perimetric segment is from said plane; said distal end being spaced inwardly a substantial distance from said first perimetric segment and effecting distortion of the trailing portion of a tang-attached article when said handle is pivoted about the first perimetric segment as a fulcrum so as to effect movement of the inserted tang and attached article towards said second compartment-forming wall.

* * * * *

UNITED STATES PATENT AND TRADEMARK OFFICE
CERTIFICATE OF CORRECTION

PATENT NO. : 4,120,397
DATED : OCTOBER 17, 1978
INVENTOR(S) : ARTHUR E. NEUMANN

It is certified that error appears in the above-identified patent and that said Letters Patent are hereby corrected as shown below:

Column 2, line 10 - "cmpartment" should be --compartment--

Column 5, line 59 - delete period (.) after "identified"

Column 5, line 66 - "unitl" should be --until--

Column 9, line 15 (claim 4) - "fromed" should be --formed--

Signed and Sealed this

Sixth Day of February 1979

[SEAL]

Attest:

RUTH C. MASON
*Attesting Officer*

DONALD W. BANNER
*Commissioner of Patents and Trademarks*